(12) United States Patent
Shay et al.

(10) Patent No.: US 10,463,685 B2
(45) Date of Patent: Nov. 5, 2019

(54) TELOMERASE MEDIATED TELOMERE ALTERING COMPOUNDS

(71) Applicant: The Board of Regents of The University of Texas System, Austin, TX (US)

(72) Inventors: Jerry W. Shay, Dallas, TX (US); Sergei M. Gryaznov, San Mateo, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 14/247,967

(22) Filed: Apr. 8, 2014

(65) Prior Publication Data

US 2014/0303239 A1  Oct. 9, 2014

Related U.S. Application Data

(60) Provisional application No. 61/809,575, filed on Apr. 8, 2013.

(51) Int. Cl.
| | | |
|---|---|---|
| A61K 31/7076 | (2006.01) | |
| A61K 45/06 | (2006.01) | |
| A61K 31/7088 | (2006.01) | |

(52) U.S. Cl.
CPC ...... *A61K 31/7076* (2013.01); *A61K 31/7088* (2013.01); *A61K 45/06* (2013.01)

(58) Field of Classification Search
CPC ............ A61K 31/7088; A61K 31/7076; A61K 45/06; A61K 2300/00
See application file for complete search history.

(56) References Cited

U.S. PATENT DOCUMENTS

2010/0323979 A1   12/2010 Weis-Amon et al. .......... 514/34

FOREIGN PATENT DOCUMENTS

| JP | 57209226 | 12/1982 |
|---|---|---|
| RU | 2158269 | 10/2000 |
| WO | WO 1992/013561 | 8/1992 |
| WO | WO 2006/114064 | 11/2006 |

OTHER PUBLICATIONS

Conroy et al., "Biosensing for the Environment and Defence," Sensors, 10,4739-4755 (2010).*
Acton, et al., "Improved antitumor effects in 3'-branched homologues of 2'-deoxythioguanosine synthesis and evaluation of thioguanine nucleosides of 2,3,-dideoxy-3-hydroxymethyl)-D-erythro-pentofuranose." J Med Chem. 22(5): 518-25, 1979.
De Lange T., "Shelterin: the protein complex that shapes and safeguards human telomeres," Genes & Development. 19:2100-10, 2005.
Fukuoka, et al., "Relation Between antitumor activity and chemical structure in some derivatives of 2-amin-6-purinethiol" GANN. 60:187-97, 1969.
Gagliano, et al., "Evaluation of beta-2/-deoxythioguanosine combined with methyl-CCNU or mitomycin in advanced colorectal cancer." Cancer Clin Trials. 4:401-5, 1981.
Greider & Blackburn, "Telomeres, telomerase and cancer," Scientific American. 274:92-7, 1996.
LePage & Khaliq, "Pharmacology and Toxicology of alpha-2'-deoxythioguanosine in cancer patients." Cancer Treat Rep. 63:53-7, 1979.
LePage, et al., "Manipulation of DNA synthesis in normal and neoplastic tissues with drugs" Advances in Enzyme Regulation. 12, 1974, pp. 373-381.
Search Report and Written Opinion in International Application No. PCT/US2014/033330 dated Nov. 21, 2014.
Tendian & Parker, "Interaction of deoxyguanosine nucleotide analogs with human telomerase" Mol Pharmacol. 57:695-99, 1999.
Viswanadhan, et al., "Analysis of the in vitro antitumor activity of novel purine-6-sulfenamide, -sulfinamind, and -sulfonamide nucleosides and certain related compounds using a computer-aided reeptor modeling procedure" J Med Chem. 34:526-32, 1991.
Wu, et al., "Telomerase antagonist imetelstat inhibits esophageal cancer cell growth and increases radiation-induced DNA breaks" Biochimica et Biophysica Acta. 1823:2130-5, 2012.
Agrawal, A., et al, "Recent Patents on Anti-Telomerase Cancer Therapy", Recent Patents on Anti-Cancer Drug Discovery, 2012, vol. 7, No. 1, pp. 102-117.
Fletcher T. M. et al. "Inhibition of Human Telomerase by 7-Deaza-2'-deoxyguanosine Nucleoside Triphosphate Analogs: Potent Inhibition by 6-thio-7-deaza-2'-deoxyguanosine 5'-triphosphate", Bioorganic Chemistry, v.29, p. 36-55 (2001).
Lauer, N.K., et al; "Absence of telomerase activity in malignant bone tumors and soft-tissue sarcomas"; Sarcoma, 6:43-46 (2002).
Paterson A. R. P. et al. "Mechanism of the Growth Inhibition Potentiation Arising from Combination of 6-Mercaptopurine with 6-(Methylmercapto) purine Ribonucleoside", Cancer Research, v.30, 2379-2387 (1970).
Yu, Chang-E, et al, "Telomerase Inhibitor GRN163L in the Treatment for Cancer", Journal of Chinese Oncology, 2013, vol. 19, No. 3, pp. 231-234 (Abstract only).
Kelland, "Overcoming the immortality of tumour cells by telomere and telomerase based cancer therapeutics—current status and future prospects," *Eur J Cancer*, 41(7):971-979, 2005.

(Continued)

*Primary Examiner* — Lawrence E Crane
(74) *Attorney, Agent, or Firm* — Parker Highlander PLLC

(57) ABSTRACT

Methods for treating a telomerase-expressing cell characterized by an over-activation of telomerase in a subject in need thereof comprising administering a pharmaceutical composition comprising a first amount of a 6-mercaptopurine analog, and a second amount of a telomerase inhibitor, wherein the first amount and the second amount together comprises an amount effective to reduce stability of telomere length and to induce cell death in the telomerase-expressing cell are provided. The methods can be used to treat patients with lung cancer, colon cancer, or cervical cancer.

8 Claims, 10 Drawing Sheets

Specification includes a Sequence Listing.

(56) References Cited

OTHER PUBLICATIONS

Office Action issued in Russian Application No. 2015147555, dated Jan. 25, 2019.
Office Action issued in Indian Application No. 9183/DELNP/2015, dated Aug. 22, 2019.

* cited by examiner

| Week / Sample | 1 | 2 | 3 | 4 | 5 | 6 | 7 | 8 | 9 | 10 | 11 | 12 | 13 | 14 | 15 | 16 |
|---|---|---|---|---|---|---|---|---|---|---|---|---|---|---|---|---|
| Control | --- | --- | --- | --- | --- | --- | --- | --- | --- | --- | --- | --- | --- | --- | --- | --- |
| A | lm | lm | lm | lm | lm | lm | lm | lm | lm | lm | lm | ■ | ■ | ■ | ■ | ■ |
| B | 6-dG | 6-dG | 6-dG | 6-dG | 6-dG | 6-dG | 6-dG | 6-dG | 6-dG | 6-dG | 6-dG | 6-dG | ■ | ■ | ■ | ■ |
| C | 6-dG | 6-dG | 6-dG | 6-dG | 6-dG | 6-dG | 6-dG | 6-dG | 6-dG | 6-dG | 6-dG | 6-dG | 6-dG | 6-dG | 6-dG | 6-dG |
| D | 6-dG | 6-dG | 6-dG | 6-dG | 6-dG | 6-dG | 6-dG | 6-dG | 6-dG | 6-dG | 6-dG | 6-dG | 6-dG | 6-dG | ■ | ■ |
| E | 6-dG | 6-dG | 6-dG | 6-dG | 6-dG | 6-dG | 6-dG | 6-dG | 6-dG | 6-dG | 6-dG | 6-dG | --- | --- | --- | --- |
| F | 6-dG | 6-dG | 6-dG | 6-dG | 6-dG | 6-dG | 6-dG | 6-dG | 6-dG | 6-dG | 6-dG | 6-dG | --- | --- | ■ | ■ |
| G | 6-dG | 6-dG | 6-dG | 6-dG | 6-dG | 6-dG | 6-dG | 6-dG | 6-dG | 6-dG | 6-dG | 6-dG | combo | combo | ■ | ■ |
| H | 6-dG | 6-dG | 6-dG | 6-dG | 6-dG | 6-dG | 6-dG | 6-dG | 6-dG | 6-dG | 6-dG | 6-dG | combo | combo | combo | combo |
| I | 6-dG | 6-dG | 6-dG | 6-dG | 6-dG | 6-dG | 6-dG | 6-dG | 6-dG | 6-dG | 6-dG | 6-dG | lm | lm | ■ | ■ |
| F | 6-dG | 6-dG | 6-dG | 6-dG | 6-dG | 6-dG | 6-dG | 6-dG | 6-dG | 6-dG | 6-dG | 6-dG | lm | lm | lm | lm |

FIG. 2

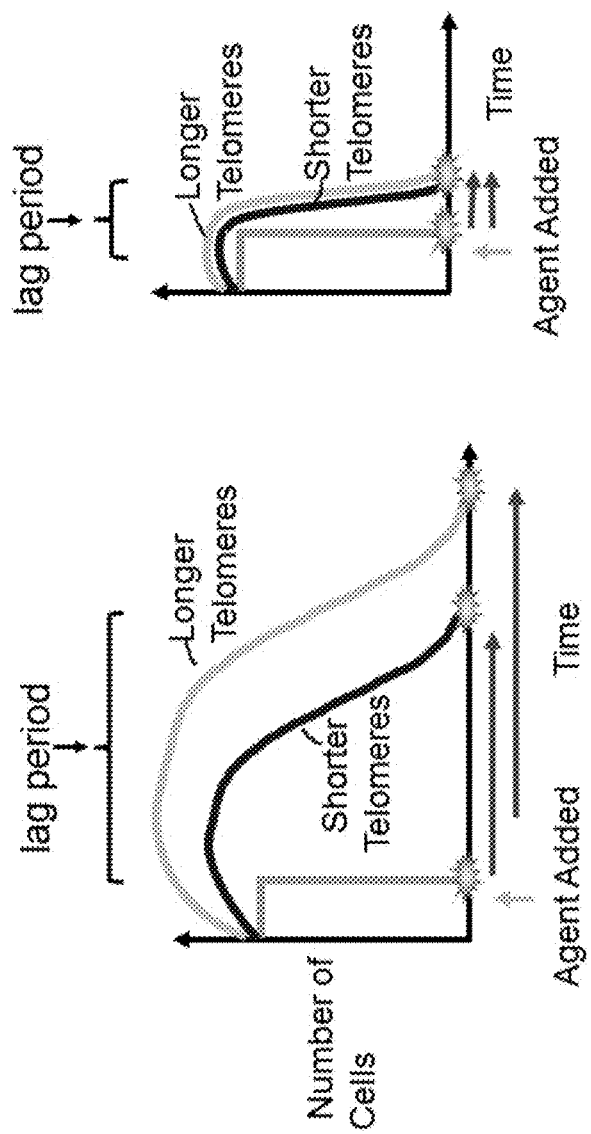

TELOMERASE MEDIATED TELOMERE ALTERING COMPOUNDS

CROSS-REFERENCE TO RELATED APPLICATIONS

This application claims the benefit of U.S. U.S. Provisional Application Ser. No. 61/809,575 filed on Apr. 8, 2013. The contents of which are hereby incorporated by reference in its entirety.

BACKGROUND

1. Field of the Invention

The present disclosure relates generally to pharmaceutical compositions and therapeutic approaches involving compounds that have an anti-cancer effect, particularly through an anti-proliferative mechanism.

2. Description of Related Art

Telomeres are highly specialized structures which are located at the very end of linear chromosomes. Normal human somatic cells progressively lose their telomeres with each cell division primarily due to the end replication problem. While the majority of normal human cells do not have telomerase activity, 85-90% of cancer cells do, which stabilizes their telomeres.

Telomeres are protective structures that are found at the end of linear eukaryotic chromosomes consisting of multiple copies of TTAGGG DNA repeats. Telomeres are associated with six proteins; TRF1, TRF2, TIN2, Rap1, TPP1 and POT1, which all together are called the shelterin complex. (de Lange T., "Shelterin: the protein complex that shapes and safeguards human telomeres," Genes & Development 2005; 19:2100-10.) The shelterin complex is present at telomeres throughout the cell cycle and have been shown to cap the chromosomal ends from being recognized as DNA damage sites.

Telomeres in all normal somatic cells undergo progressive shortening with each cell division due to the end replication problem, eventually resulting in cellular senescence. However, replication-dependent telomeric shortening can be counteracted by the ribonucleoprotein enzyme, telomerase. Telomerase is a cellular reverse transcriptase that adds TTAGGG repeats to the end of linear chromosomes. Telomerase has two components, hTERT (telomerase catalytic protein component) and hTR or hTERC (telomerase functional or template RNA component). (Greider C W and Blackburn E H, "Telomeres, telomerase and cancer," Scientific American. 1996; 274:92-7.) While most normal somatic human cells do not have telomerase activity, it is detected, almost universally, in primary human cancer cells (~85-90%). Thus, the progressive shortening in normal cells without telomerase activity provide an initial barrier for tumorigenesis.

Therefore, in cancer cells telomerase and telomeres represent attractive almost universal targets for therapeutic approaches. Because most normal somatic cells do not have telomerase activity, treatments that selectively target telomerase activity can be beneficial. In addition, treatments that can interfere with telomere sequencing during telomerase activity to interfere with the structure or function of the shelterin complex can also be beneficial.

SUMMARY

The present disclosure relates to the use of the compound 6-mercaptopurine ribonucleoside and analogues thereof for the treatment of tumors, cancer, and hyperproliferative diseases. Specifically, compounds of the present disclosure can be converted into telomere substrates in vivo and can be recognized by telomerase for incorporation into telomeres of telomerase active cells, leading to induction of cell death of the telomerase active cells. While not wishing to be bound by any particular theory, incorporation of the described compounds into the telomere is believed to be an immediate teloemere DNA chain terminator and/or recognized as having telomeric DNA damage due to the altered telomere structure.

In accordance with the present disclosure, a compound according to Formula I below can be administered to a subject:

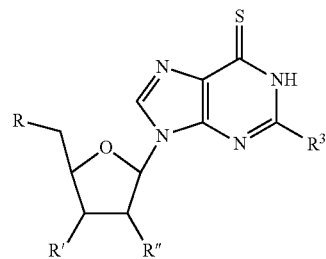

where R can be an H, hydroxyl group, an amino group, an alkyl amino group, a fluoride, an acyl group, a $C_1$-$C_{20}$ alkyl or ether group, a phosphate, diphosphate, triphosphate, phosphonate, or a phosphodiester group; where R' can be an H, a hydroxyl group, flouride group, a $C_1$-$C_{20}$ alkyl or ether group; where R" can be a hydroxyl group, a flouride, or an amino group in the ribo or arabino configuration; where $R^3$ can be an amino group or a alkyl-amino group; and pharmaceutically acceptable salts, solvates or polymorphs thereof. In various embodiments, R. is OH, R' is a hydroxyl group, and R" is H and such compounds are referred to herein as 6-thio-2'-deoxyguanosine.

In accordance with the present disclosure, a compound according to Formula II below can be administered to a subject:

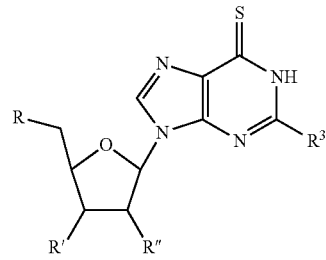

where R can be an H, an acyl group, a $C_1$-$C_{20}$ alkyl or ether group, a phosphate, diphosphate, triphosphate, phosphonate, or a phosphodiester group; where R' can be an H, a hydroxyl group, flouride, a $C_1$-$C_{20}$ alkyl or ether group; where R" can be a hydroxyl group, a flouride, or an amino group in the ribo or arabino configuration; where $R^3$ can be an amino group or a alkyl-amino group; and pharmaceutically acceptable salts, solvates or polymorphs thereof. In various embodiments, R is H, R' is a hydroxyl group, and R" is H.

In accordance with the present disclosure, a pharmaceutical composition can comprise a compound according to Formula III below can be administered to a subject:

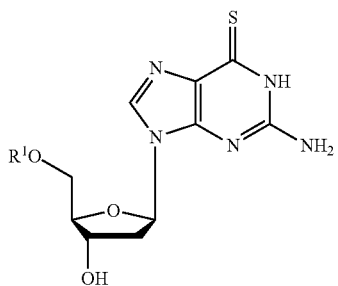

where R[1] can be an H, or —C(O)(CH$_2$)CH$_3$ where n=6-16 and such compounds are referred to herein as 6-thio-2'-deoxyguanosine.

Pharmaceutical compositions comprising an anti-cancer effective amount of one or more of the compounds of Formula I, II, or III, optionally in combination with an effective amount of at least one additional anti-cancer agent or at least one carrier, additive or excipient are additional aspects of the present disclosure.

Further aspects of the present disclosure relate to methods for treating cancer and other hyperproliferative diseases, including tumors, especially malignant tumors and cancer, and any cell which possesses an over-activation of telomerase.

Other aspects of the present disclosure comprise a method of treatment comprising administering an effective amount of 6-mercaptopurine ribonucleoside analogue according to the present disclosure and administering a second pharmaceutical composition comprising another anti-cancer agent. Administration can occur simultaneously, in sequential stages, or be administered stages wherein the stages at least partially overlap in time or are spaced apart by an certain interval of time. The multiple anti-cancer agent treatment can provide an additive effect or further a synergistic enhancement of the anticancer activity of one or both of the anti-cancer agents.

Embodiments discussed in the context of methods or compositions of the disclosure can be employed with respect to any other method or composition described herein. Thus, an embodiment pertaining to one method or composition may be applied to other methods and compositions of the invention as well. As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.]

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 2. Time table of HCT116 cells treatment protocols with no drug (--), 6-thio-dG (6dG), GRN163L (Im) or combination of 6-thio-dG and GRN163L (combo). Each week 1×10$^6$ cells/sample were collected for TRF analysis. HCT116 cells were treated 10 μM 6-thio-dG for 12-16 weeks. After treating with 10 μM 6-thio-dG for 12 weeks, the cells were treated with combination of 10 μM 6-thio-dG and 3 μM GRN163L for 2-4 weeks or only GRN163L for 2-4 weeks or cessation of drug for 2-4 weeks. (Control; untreated). TRF analysis was used to ascertain telomere shortening at the end of each treatment protocol.

FIGS. 3A and 3B. (A) An comparative line graph showing the lag period between administration of a telomerase inhibitor and cell death for cells with short telomeres and long telomeres. (B) An comparative line graph showing the lag period between administration of a telomere-altering compounds and cell death for cells with short telomeres and long telomeres.

DESCRIPTION OF ILLUSTRATIVE EMBODIMENTS

Figure 1A:
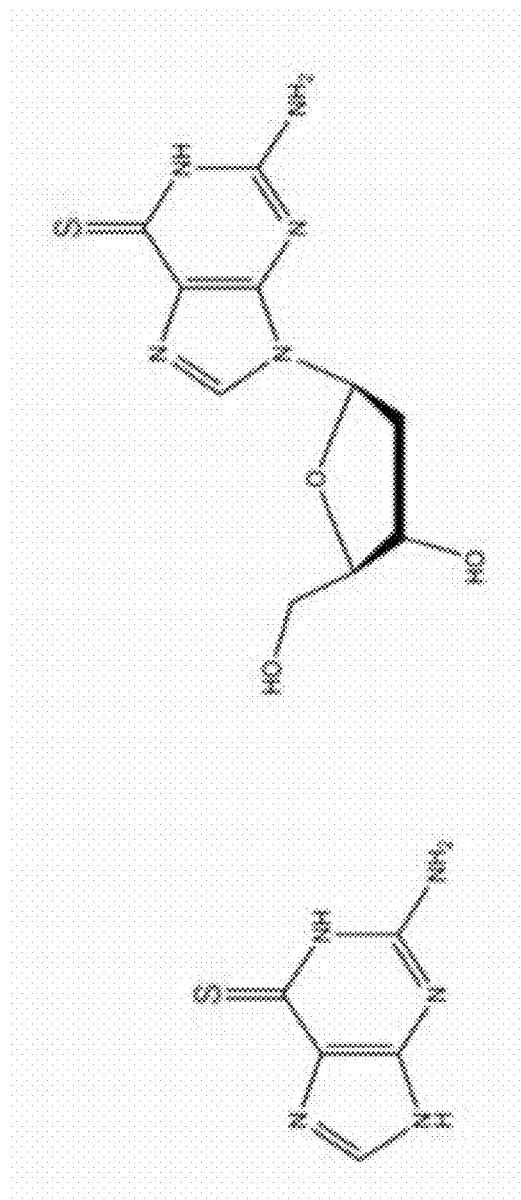
FIG. 1A The chemical structures of 6-thioguanine (6-thio-G) and 6-thio-deoxyguanosine (6-thio-dG).

The present disclosure is directed toward pharmaceutical compositions and treatment methods using 6-thioguanosine analogues as telomere disrupting compounds. These analogues can be converted in vivo to 5'-triphosphate telomerase substrates, e.g., 2'-deoxyguanosine 5'-triphosphate. The described substrates can be incorporated into telomeres causing telomere shortening, telomere dysfunction, or both.

More specifically, analogues of the present disclosure can act as a telomere targeting molecule in cancer cells, but generally not (or much less so) in normal telomerase activity negative cells. This generally selective treatment results from the fact that analogues of the present disclosure targets cancer cells expressing telomerase. Treatment of telomerase active cells with the Formula I, II, and/or III compound can result in acute cell death in at least a portion or majority of the active cells. The cell death can be the effect of progressive telomere shortening or telomere dysfunction, e.g., causing a telomere-associated DNA damage, since some guanine bases will be replaced by 6-thio-guanine counterparts and inducing a DNA damage response such as through the alteration of the structure and function of the shelterin complex. Further, compounds of the present disclosure may not cause any or may cause only a slight inhibition of telomerase activity in vitro, as tested by Telomeric Repeat Amplification Protocol (TRAP) assay. Lastly, compounds of the present disclosure may cause genomic DNA damage. Hence, administration of the various pharmaceutical compositions in accordance with the present disclosure represent a an approach to treatment of telomerase positive human cancers based on a bifunctional mechanism of action characterized as i) acute cytotoxicity derived from anti-metabolic properties and incorporation into genomic DNA and ii) telomeric DNA modification and shortening. The present disclosure is also directed to methods of treatment comprising a combination treatment plan or a coadministration of second pharmaceutical composition.

In accordance with the present disclosure, a pharmaceutical composition can comprise the compound 6-mercaptopurine ribonucleoside and analogues thereof for the treatment of tumors, cancer, and hyperproliferative diseases. In various embodiments, a pharmaceutical composition can comprise a compound according to Formula I below can be administered to a subject:

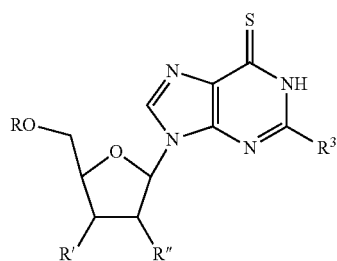

where R can be an H, hydroxyl group, an amino group, an alkyl amino group, a fluoride, an acyl group, a $C_1$-$C_{20}$ alkyl or ether group, a phosphate, diphosphate, triphosphate, phosphonate, or a phosphodiester group; where R' can be an H, a hydroxyl group, flouride group, a $C_1$-$C_{20}$ alkyl or ether group; where R" can be a hydroxyl group, a flouride, or an amino group in the ribo or arabino configuration; where $R^3$ can be an amino group or a alkyl-amino group; and pharmaceutically acceptable salts, solvates or polymorphs thereof, and such compounds are referred to herein as 6-thio-2'-deoxyguanosine. In various embodiments, R is H, R' is a hydroxyl group, and R" is H.

In various embodiments, a pharmaceutical composition to be administered to a subject can comprise a compound according to Formula II below:

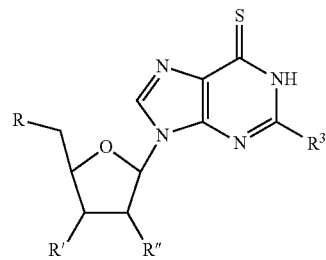

where R can be an H, an acyl group, a $C_1$-$C_{20}$ alkyl or ether group, a phosphate, diphosphate, triphosphate, phosphonate, or a phosphodiester group; where R' can be an H, a hydroxyl group, flouride, a $C_1$-$C_{20}$ alkyl or ether group; where R" can be a hydroxyl group, a flouride, or an amino group in the ribo or arabino configuration; where $R^3$ can be an amino group or a alkyl-amino group; and pharmaceutically acceptable salts, solvates or polymorphs thereof. In various embodiments, R. is H, R' is a hydroxyl group, and R" is H and such compounds are referred to herein as 6 mercaptopurine ribonucleoside analogues.

In various embodiments, a pharmaceutical composition can comprise a compound according to Formula III below can be administered to a subject:

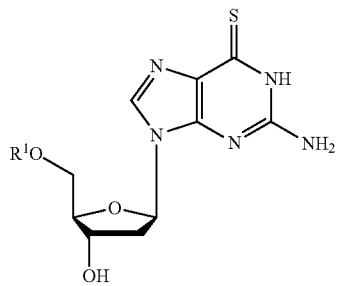

where $R^1$ can be an H, or —C(O)(CH$_2$)$_n$CH$_3$ where n=6-16 and pharmaceutically acceptable salts, solvates or polymorphs thereof, and such compounds are referred to herein as 6-thio-2'-deoxyguanosine.

The term "alkyl" shall mean within its context a $C_1$-$C_{20}$, preferably a $C_1$-$C_{10}$ linear, branch-chained or cyclic fully saturated hydrocarbon radical, which may be optionally substituted, such as with a phenyl group, for example. The term alkyl shall also embrace aralkyl groups such as benzyl groups, which phenyl group may be optionally substituted. Functional groups not expressly provided are understood to one of a hydrogen or alkyl group as defined herein. The term "ether" shall mean a $C_1$ to $C_{20}$ ether group, formed from an oxygen and an alkyl group at a position on the sugar moiety of compounds according to the present invention, and preferably contains at least one oxygen group within the alkyl chain.

The term "acyl" is used throughout the specification to describe a group at the 5' position of the nucleoside analog (e.g., at the free hydroxyl position in the sugar unit) which contains a $C_1$ to $C_{20}$ linear, branched or cyclic alkyl chain or a related group as otherwise described herein. The acyl group at the 5' position (R), in combination with the corresponding hydroxyl group results in an ester, which, after administration, may be cleaved to produce the free nucleoside form of the present invention.

The term "phosphodiester" describes mono-phosphate groups at the 5' position of the sugar unit which are diesterified such that the phosphate group is rendered neutral, i.e., has a neutral charge.

Modifications of the Formula I, II, or III compounds, particularly at the 5' position, can affect the solubility, bioavailability and rate of metabolism of the active species, thus providing control over the delivery of the active species. Further, the modifications can affect the anticancer activity of the compound, in some cases increasing the activity over the native guanine compound. This can be assessed by preparing the derivative and testing its anticancer activity according to the methods described herein, or other method known to those skilled in the art.

As used herein, "treatment" and "treating" refer to administration or application of a therapeutic agent to a subject or performance of a procedure or modality on a subject for the purpose of obtaining a therapeutic benefit with respect to a disease or health-related condition or a prophylactic effect with respect to a disease or health-related condition. For example, a treatment may include administration of a pharmaceutically effective amount of a 2-amino-6-mercaptopurine ribonucleoside analogue to a subject having cancer cells. As used herein, the term "therapeutic benefit" or "therapeutically effective" refers to a promotion or enhancement of the well-being of the subject or increases the likelihood thereof with respect to the medical treatment of a disease or health related condition. This includes, but is not limited to, a reduction in the frequency or severity of the signs or symptoms of a disease. For example, treatment of cancer may involve, for example, a reduction in the size of a tumor, a reduction in the invasiveness of a tumor, reduction in the growth rate of the cancer, senescence of a portion of cells that exhibit an abnormal activation of telomerase, or prevention of metastasis or recurrence. Treatment of cancer may also refer to prolonging survival of a subject with cancer. As used herein, the phrase "effective amount" describes an amount of a compound which, in context, is used to produce or affect a therapeutic benefit.

As used herein, the phrase "anti-cancer effect" refers to an effect that can include one or more of inhibiting further growth of tumor or cancer cells; reducing the likelihood or eliminating metastasis; contributing to cell death in the tumor, cancer cells, or other cells with an abnormal activation of telomerase; resulting in a shrinkage of the tumor or a reduction in the number of cancer cells; or preventing the regrowth of a tumor or cancer after the patient's tumor or cancer is in remission. Compositions or derivatives thereof in accordance with the present disclosure exhibit an anti-cancer effect.

A "subject" refers to either a human or non-human, such as primates, mammals, and vertebrates. In particular embodiments, the subject is a human.

In accordance with various embodiments, a method of treatment can comprise administering to a subject a pharmaceutical composition comprising one or more 6-mercaptopurine ribonucleoside or analogues thereof, e.g., a Formula I, II, and/or III compound. The method can be used in the treatment of a cancer or other hyperproliferative disease state or in the treatment of cells exhibiting pronounced telomerase activity. The cancer may be a solid tumor, metastatic cancer, or non-metastatic cancer. In certain embodiments, the cancer may originate in the bladder, blood, bone, bone marrow, brain, breast, colon, esophagus, duodenum, small intestine, large intestine, colon, rectum, anus, gum, head, kidney, liver, lung, nasopharynx, neck, ovary, prostate, skin, stomach, testis, tongue, or uterus. A tumor can comprise a malignant or benign growth or tumefacent.

The cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; non-encapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; hodgkin's disease; hodgkin's; paragranuloma; malignant lymphoma, small lymphocytic; malignant lymphoma, large cell, diffuse; malignant lymphoma, follicular; mycosis fungoides; other specified non-hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

Nonetheless, it is also recognized that the present invention may also be used to treat a non-cancerous disease associated with activation of telomerase in inflammatory (leukocyte) cells (e.g., a fungal infection, a bacterial infection, a viral infection, acute and chronic inflammatory diseases such as inflammatory bowel disease (Crohn's disease, ulcerative colitis), rheumatoid arthritis and/or a neurodegenerative disease associated with inflammation).

A hyperproliferative disease state comprises a disease state in which cells are growing in an uncontrolled manner, whether that growth is cancerous or not. Such a disease state may be reflected in psoriasis, genital warts or other hyperproliferative cell growth diseases, including hyperproliferative keratinocyte diseases including hyperkeratosis, ichthyosis, keratoderma or lichen planus, all of which disease states may be treated using compounds according to the present invention. The method aspect includes treating hyperproliferative diseases including psoriasis, genital warts and hyperproliferative cell growth diseases, including hyperproliferative keratinocyte diseases such as hyperkeratosis, ichthyosis, keratoderma or lichen planus and other chronic inflammatory diseases such as osteoarthritis hepatitis C virus (HCV) infections, the methods comprising administering to a patient in need thereof an effective amount of a Formula I, II, and/or III compound according to the present disclosure, optionally in combination with at least one additional anticancer agent, optionally in combination with a pharmaceutically acceptable carrier, additive or excipient.

Pharmaceutical compositions in accordance with certain embodiments of the present disclosure can comprise an effective amount of one or more a Formula I, II, III, IV, or V compound and optionally an additional active ingredient dissolved or dispersed in a pharmaceutically acceptable carrier.

As used herein, the term "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. The term "pharmaceutically acceptable carrier," means a pharmaceutically acceptable material, composition or vehicle, such as a liquid or solid filler, diluent, excipient, solvent or encapsulating material, involved in carrying or transporting a chemical agent.

The pharmaceutical composition can be administered to a subject by any method known to those of ordinary skill in the art. Examples may include, but not be limited to administration intravenously, intradermally, intrathecally, intraarterially, intraperitoneally, intramuscularly, subcutaneously; orally, intrarectally, mucosally (intranasal, intravaginal, etc.), topically (i.e., transdermally), locally, via inhalation (e.g., aerosol inhalation), via injection, via infusion, via continuous infusion, via localized perfusion bathing target cells directly, via a catheter, via a lavage, in creams, in lipid compositions (e.g., liposomes), or by other method or any combination of the forgoing as would be known to one of ordinary skill in the art (see, for example, Remington's Pharmaceutical Sciences, 18th Ed. Mack Printing Company, 1990, incorporated herein by reference).

The pharmaceutical composition may be formulated into a composition in a free base, neutral or salt form. Pharmaceutically acceptable salts, include the acid addition salts, e.g., those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Upon formulation, solutions will be administered in a manner compatible with the dosage formulation and in such amount as is therapeutically effective.

In embodiments where the composition is in a liquid form, a carrier can be a solvent or dispersion medium comprising but not limited to, water, ethanol, polyol (e.g., glycerol, propylene glycol, liquid polyethylene glycol, etc.), lipids (e.g., triglycerides, vegetable oils, liposomes) and combinations thereof. The proper fluidity can be maintained, for example, by the use of a coating, such as lecithin; by the maintenance of the required particle size by dispersion in carriers such as, for example liquid polyol or lipids; by the use of surfactants such as, for example hydroxypropylcellulose; or combinations thereof such methods. It may be preferable to include isotonic agents, such as, for example, sugars, sodium chloride or combinations thereof.

The actual dosage amount of a composition in accordance with certain embodiments of the present disclosure administered to subject can be determined by physical and physiological factors such as the specific compound employed, the age, general health of the subject, diet, body weight, severity of condition, the type of disease being treated, previous or concurrent therapeutic interventions, idiopathy of the patient, absorption rates, distribution rates, inactivation rates, excretion rates, time of administration, the route of administration, and on the, judgment of the person supervising the administration. Depending upon the dosage and the route of administration, the number of administrations of a preferred dosage, and/or an effective amount may vary according to the response of the subject. The active ingredient may be administered at once, or may be divided into a number of smaller doses to be administered at varying intervals of time. As such, it is understood that for any particular subject, specific dosage regimens could be adjusted over time according to the individual need and the professional judgment of the person administering or supervising the administration of the compositions, and that the concentration ranges set forth herein are exemplary only and are not intended to limit the scope or practice of the claimed composition.

The Formula I, II, and/or III compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 100 mg/kg, preferably 0.1 to 50 mg/kg per day, more generally 0.5 to about 25 mg per kilogram body weight of the subject per day. By way of non-limiting example, a typical dosage can range from 0.01-20% wt/wt in a suitable carrier. Similarly, the compound can be administered in any suitable unit dosage form, including but not limited to one containing less than 1 mg, 1 mg to 3000 mg, or 5 to 1000 mg of active ingredient per unit dosage form.

Compositions may be administered on an ongoing or continuous basis; on an as needed basis; or 1, 2, 3, 4, 5, 6, 7, 8, 9, 10, 11, 12, 13, 14, 15, 16, 17, 18, 19, 20 or more times. They may be administered every 1, 2, 3, 4, 5, 6, 7, 8, 9, 10, 11, 12, 13, 14, 15, 16, 17, 18, 19, 20, 21, 22, 23, 24 hours, or 1, 2, 3, 4, 5, 6, 7 days, or 1, 2, 3, 4, 5 weeks, or 1, 2, 3, 4, 5, 6, 7, 8, 9, 10, 11, 12 months or more. (or any value derivable therein). Similarly, it is specifically contemplated that the composition may be administered once daily, twice daily, three times daily, four times daily, five times daily, or six times daily (or any range derivable therein) and/or as needed to the patient. A dose may be first administered before or after detection of a disease or health related condition or subsequent to a test where no disease indicators are detected. In some embodiments, the patient can be administered a composition in cycles of days or weeks and in between each cycle, no drug is administered between cycles. The time between each cycle can be days or weeks, e.g., 2-8 days/weeks. In some embodiments, the patient is administered the composition for a certain period of time or with a certain number of doses after there is no detectable presence of a disease or disorder.

Similarly, in various embodiments, the composition may be administered to (or taken by) the patient about, at least about, or at most about 0.01-1000 µl/min, µl/hour, µl/day, µl/week, µl/month, ml/min, ml/hour, ml/day, ml/week, ml/month, µg/min, µg/hour, µg/day, µg/week, µg/month, mg/min, mg/hour, mg/day, mg/week, mg/month or any range derivable therein.

In order to increase the effectiveness a treatment, it may be desirable to combine compositions of the present disclosure with a second treatment or pharmaceutical composition. For example, a method of use can further include administration of a second pharmaceutical composition comprising an anti-cancer agent or other agent effective in the treatment of hyperproliferative disease. An anti-cancer agent can negatively affect cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, a second pharmaceutical composition can be administered in an effective amount or combined effective amount to kill or inhibit proliferation of certain cells.

In various embodiments, a method of treatment can comprise a simultaneous coadministration. This process may involve administration at the same time. This can be achieved by contacting the cell with a single composition or pharmaceutical formulation that includes both a Formula I, II, and/or III compound and another anti-cancer agent, or by contacting the cell with two distinct compositions or formulations, at the same time, wherein one composition includes the Formula I, II, and/or III compound and the other includes the second agent(s). Similarly, two compositions can be administered not at the same time but in temporal proximity to each other, e.g., on the same day or within the same week.

In various embodiments a method of treatment can comprise a first stage wherein a pharmaceutical composition comprising a Formula I, II, and/or III compound is administered and a second stage where a second pharmaceutical composition is administered. The first stage and the second stage may be sequential in time, spaced apart in time (minutes, days, weeks, or months), or overlapping in time. In addition, the sequential order of treatment stages can be reversed or repeated.

To be sure, any combination of treatment stages may be employed. By way of example, administration of a Formula I, II, and/or III compound is "A" and the treatment with a secondary agent is "B":

A/B/A B/A/B B/B/A A/A/B A/B/B B/A/A A/B/B/B B/A/B/B
B/B/B/A B/B/A/B A/A/B/B A/B/A/B A/B/B/A B/B/A/A
B/A/B/A B/A/A/B A/A/A/B B/A/A/A A/B/A/A A/A/B/A

In the context of the present disclosure, it is contemplated that administration of a pharmaceutical composition comprising a Formula I, II, and/or III compound could be used in conjunction with a treatment B, such as gene therapy, chemotherapeutic, radiotherapeutic, or immunotherapeutic intervention, in addition to other pro-apoptotic or cell cycle regulating agents. It also is contemplated that various standard therapies, as well as surgical intervention, may be applied in combination with the described telomere shortening and telomere dysfunction-inducing therapy.

a. Chemotherapy

Chemotherapies include, for example, cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, gemcitabine, navelbine, farnesyl-protein transferase inhibitors, transplatinum, 5-fluorouracil, vincristin, vinblastin and methotrexate, or any analog or derivative variant of the foregoing.

b. Radiotherapy

Radiotherapies can cause DNA damage and include what are commonly known as—rays, X-rays, and/or the directed delivery of radioisotopes to tumor cells. Other forms of DNA damaging factors are also contemplated such as microwaves and UV-irradiation.

c. Immunotherapy

Immunotherapeutics, generally, rely on the use of immune effector cells and molecules to target and destroy cancer cells. Immunotherapy, thus, could be used as part of a combined therapy, in conjunction with the administration of a pharmaceutical composition comprising a Formula I, II, and/or III compound. Immunotherapy modality relates to the targeting of the tumor cell through some marker of the tumor cell that is amenable to targeting, i.e., is not present on the majority of other cells. Many tumor markers exist and any of these may be suitable for targeting with a second treatment modality in the context of the present disclosure. Common tumor markers include carcinoembryonic antigen, prostate specific antigen, urinary tumor associated antigen, fetal antigen, tyrosinase (p9'7), gp68, TAG-72, HMFG, Sialyl Lewis Antigen, MucA, MucB, PLAP, estrogen receptor, laminin receptor, erb B and p155.

d. Genes

In yet another embodiment, the secondary treatment B is a gene therapy in which a therapeutic polynucleotide encoding all of part of a polypeptide is administered before, after, or at the same time as a pharmaceutical composition comprising a Formula I, II, and/or III compound. Delivery of vector encoding a certain gene product(s) related to the particular disease or health related condition can have a combined therapeutic effect, e.g., anti-proliferative effect, on target tissues.

e. Surgery

Curative surgery is a cancer treatment that can be used in conjunction with a pharmaceutical composition comprising a Formula I, II, and/or III compound. Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and miscopically controlled surgery (Mohs' surgery). It is further contemplated that composition of the present disclosure can be administered in conjunction with removal of superficial cancers, precancers, or incidental amounts of normal tissue. Upon excision of part of all of cancerous cells, tissue, or tumor, a cavity may be formed in the body. Treatment may be accomplished by administration of a pharmaceutical composition comprising a Formula I, II, III, IV, and/or V compound.

f. Other Anti-Cancer Agents

It is contemplated that other anti-cancer agents may be used in combination with Formula I, II and/or III compositions of the present disclosure to additively or synergistically enhance the therapeutic efficacy of treatment.

These additional agents include immunomodulatory agents, agents that affect the upregulation of cell surface receptors and GAP junctions, cytostatic and differentiation agents, inhibitors of cell adhesion, or agents that increase the sensitivity of the hyperproliferative cells to apoptotic inducers. Immunomodulatory agents include tumor necrosis factor; interferon alpha, beta, and gamma; IL-2 and other cytokines; F42K and other cytokine analogs; or MIP-1, MIP-1beta, MCP-1, RANTES, and other chemokines. It is further contemplated that the upregulation of cell surface receptors or their ligands such as Fas/Fas ligand, DR4 or DR5/TRAIL would potentiate the apoptotic inducing abilities of the present disclosure by establishment of an autocrine or paracrine effect on hyperproliferative cells. Increases intercellular signaling by elevating the number of GAP junctions would increase the anti-hyperproliferative effects on the neighboring hyperproliferative cell population. In other embodiments, cytostatic or differentiation agents can be used in combination with the present invention to improve the anti-hyperproliferative efficacy of the treatments. Inhibitors of cell adhesion are contemplated to improve the efficacy of the present invention. Examples of cell adhesion inhibitors are focal adhesion kinase (FAKs) inhibitors and Lovastatin. It is further contemplated that other anti-cancer agents that increase the sensitivity of a hyperproliferative cell to apoptosis, such as telomerase inhibitors like imetelstat sodium and signal transduction inhibitors like the antibody c225, could be used in combination with the present invention to improve the treatment efficacy. As shown in the Example section, a clinically relevant combination of 6-thio-deoxyguanosine and imetelstat sodium showed additive effects on telomere shortening in HCT116 cells. In various embodiments, a method of treatment can comprise administration of telomere targeting/modifying composition such as a Formula I, II, and/or III compound and a telomerase inhibiting composition such as imetelstat sodium, whether simultaneously, sequentially or both. Such embodiments can have an additive effect on telomere shortening.

Lastly, additional agents can also include anti-cancer agents which are broadly characterized as anti-metabolites, inhibitors of topoisomerase I and II, alkylating agents and microtubule inhibitors (e.g., taxol). Anti-cancer agents for use in the present invention include, for example, Aldesleukin; Alemtuzumab; alitretinoin; allopurinol; altretamine; amifostine; anastrozole; arsenic trioxide; Asparaginase; BCG Live; bexarotene capsules; bexarotene gel; bleomycin; busulfan intravenous; busulfan oral; calusterone; capecitabine; carboplatin; carmustine; carmustine with Polifeprosan 20 Implant; celecoxib; chlorambucil; cisplatin; cladribine; cyclophosphamide; cytarabine; cytarabine liposomal; dacarbazine; dactinomycin; actinomycin D; Darbepoetin alfa; daunorubicin liposomal; daunorubicin, daunomycin; Denileukin diftitox, dexrazoxane; docetaxel; doxorubicin; doxorubicin liposomal; Dromostanolone propionate; Elliott's B Solution; epirubicin; Epoetin alfa estramustine; etoposide phosphate; etoposide (VP-16); exemestane; Filgrastim; floxuridine (intraarterial); fludarabine; fluorouracil (5-FU); fulvestrant; gemtuzumab ozogamicin; goserelin acetate; hydroxyurea; Ibritumomab Tiuxetan; idarubicin; ifosfamide; imatinib mesylate; Interferon alfa-2a; Interferon alfa-2b; irinotecan; letrozole; leucovorin; levamisole; lomustine (CCNU); mechlorethamine (nitrogen mustard); megestrol acetate; melphalan (L-PAM); mercaptopurine (6-MP); mesna; methotrexate; methoxsalen; mitomycin C; mitotane; mitoxantrone; nandrolone phenpropionate; Nofetumomab; LOddC; Oprelvekin; oxaliplatin; paclitaxel; pamidronate; pegademase; Pegaspargase; Pegfilgrastim; pentostatin; pipobroman; plicamycin; mithramycin; porfimer sodium; procarbazine; quinacrine; Rasburicase; Rituximab; Sargramostim; streptozocin; talbuvidine (LDT); talc; tamoxifen; temozolomide; teniposide (VM-26); testolactone; thioguanine (6-TG); thiotepa; topotecan; toremifene; Tositumomab; Trastuzumab; tretinoin (ATRA); Uracil Mustard; valrubicin; valtorcitabine (monoval LDC); vinblastine; vinorelbine; zoledronate; and mixtures thereof, among others.

Hormonal therapy may also be used in combination with the administration of a pharmaceutical composition comprising a Formula I, II, and/or III compound. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Preparation and Administration of the Active Compounds and Compositions Formula I, II, or III can be prepared according to the methods disclosed in detail in the art or by any other method known to those skilled in the art. In the case of compounds which contain two active agents, linking of a Formula I, II, and/or III compound to another active agent may be readily accomplished following standard techniques. Appropriate blocking groups and agents to form the linking groups may be used readily.

Hormonal therapy may also be used in combination with the administration of a pharmaceutical composition comprising a Formula I, II, and/or III compound. The use of hormones may be employed in the treatment of certain cancers such as breast, prostate, ovarian, or cervical cancer to lower the level or block the effects of certain hormones such as testosterone or estrogen. This treatment is often used in combination with at least one other cancer therapy as a treatment option or to reduce the risk of metastases.

Preparation and Administration of the Active Compounds and Compositions Formula I, II, or III can be prepared according to the methods disclosed in detail in the art or by any other method known to those skilled in the art. In the case of compounds which contain two active agents, linking of a Formula I, II, and/or III compound to another active agent may be readily accomplished following standard techniques. Appropriate blocking groups and agents to form the linking groups may be used readily.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Materials and Methods:
Cell Lines

HCT116 represents a human colon cancer cells, A549 models human lung epithelial cancer cells, H2882 models human lung epithelial cancer cells, HCC2429 models human lung epithelial cancer cells, HCC827 models human lung epithelial cancer cells, HCC15 models human lung epithelial cancer cells, H2087 models human lung epithelial cancer cells, HCC4017 models human lung epithelial cancer cells, HCC515 models human lung epithelial cancer cells, H2009 models human lung epithelial cancer cells, BJ-hTERT cells model telomerase expressing normal human fibroblast cells, and BJ human fibroblasts (telomerase silent) were grown in a Media X (Hyclone, Logan, Utah) supplemented with 10% cosmic calf serum (Hyclone).

Drug Preparation 6-thio-dG (Metkinen Oy, Kuopio, Finland) was dissolved in DMSO/water (1:2), 6-thio-G (Sigma, St Louis, Mo.) was dissolved in serum free medium, and GRN163L (Geron Corporation, Menlo Park, Calif.) was dissolved in phosphate buffer saline (PBS) to prepare 50 mM or 10 mM stock solutions, which were frozen at −80° C. After stock solutions were prepared, they were aliquoted into 1 mM solutions, which were further diluted as needed for in vitro treatment experiments.

GRN163L (Imetelstat sodium) is a 13-mer thio-phophoramidate oligonucleotide with the following sequence: 5'-TAGGGTTAGACAA-3' (SEQ ID NO: 1). Imetelstat has a polmitoyl group at the 5'-end, that helps the oligonucleotide to pass through cell membranes. The compound is complementary to the template region of human telomerase RNA subunit (hTR), and it is a highly potent direct and competitive inhibitor of telomerase. Tumor cell line treatment with imetelstat results in telomerase inhibition and progressive telomere shorting, leading to cell senescence or apoptosis in vitro.

Long-Term Cell Culture Studies

For long-term cellular experiments, HCT116 (1,000 cells/cm$^2$) and BJ (10,000 cells/cm$^2$) cells were fed with 6-thio-dG (1, 3, 10 µM) containing medium every three days. The cells were counted and replated every week for 10-16 weeks. Additionally, HCT116 cells (1,000 cells/cm$^2$) were fed with 6-thio-G (1, 3, 10 µM) every three days and each week cells were counted, collected for TRF (Telomere Restriction Fragment) analysis and replated. HCT116 cells, following treatment with 10 µM 6-thio-dG for 12 weeks, were then treated with a combination of 10 µM 6-thio-dG and 304 GRN163L for 2-4 weeks.

Telomerase Activity Assay

Telomerase activity was measured by the TRAP assay (Telomeric Repeat Amplification Protocol as described in Shay J. W. and Bacchetti S., "A survey of telomerase activity in human cancer," European Journal of Cancer 1997; 33:787-91.). Briefly, HCT116 cells were treated with 1 or 10 µM 6-thio-dG for 1-12 weeks. 1×10$^5$ cells were collected and lysed with ice-cold NP-40 lysis buffer (10 mM Tris-HCl pH 8.0, 1.0 mM MgCl2, 1 mM EDTA, 1% NP-40, 0.25 mM sodium deoxycholate, 10% glycerol, 150 mM NaCl, 5 mM β-mercaptoethanol) for 30 min. One microliter cellular lysate for 2500 cells was used for each reaction. Hela cells were used as a positive control and lysis buffer was used as a negative control. Samples were prepared and then the telomerase extension products were amplified using PCR (95° C. for 5 min to inactivate telomerase, then 95° C. for 30 sec, 52° C. for 30 sec, 72° C. for 30 sec; 24 cycles). Samples were run on a 10% non-denaturating acrylamide gel and visualized using a Typhoon PhosphorImager scanner system (Molecular Dynamics, GE Healthcare, Piscataway, N.J.) that is capable of reading Cy5 fluorescence.

Telomere Length Assay (TRF, Terminal Restriction Fragment)

1×10$^6$ cells were collected and washed with PBS. DNA was isolated using the manufacturer's instructions (Qiagen, Valencia, Calif.). 2.5 µg DNA was digested with six different restriction enzymes (HhaI, HinfI, MspI, HaeIII, RsaI, AluI) (New England Bio, Ipswich, Mass.) and incubated at 37° C. overnight. Digested DNA was separated on a 0.7% agarose gel overnight at 70 V. The terminal restriction fragment (TRF) gel was denatured for 20 min in denaturing solution (0.5 M NaOH, 1.5 M NaCl, pH 13.2) and dried on Whatman 3 MM paper under vacuum for 3 hours at 56° C. The gel was neutralized for 15 minutes in neutralization buffer (1.5 M NaCl, 0.5 M Tris-HCl, pH 8.0) and then probed with a radiolabeled telomeric probe (C-rich) for 16 hours at 42° C. in 5×SSC buffer, 5×Denhardt's solution, 10 mmol/L Na$_2$HPO$_4$, and 1 mmol/L Na$_2$H$_2$P$_2$O$_7$. The gel was washed once with 2×SSC, 0.1% SDS, twice with 0.5×SSC, 0.1% SDS and then twice with 0.5×SSC, 1% SDS at room temperature for 15 min. Gels were exposed to a PhosphorImager screen overnight and analyzed using a Typhoon PhosphorImager scanner system (Molecular Dynamics).

Telomere Dysfunction Induced Foci (TIF) Assay

The TIF assay is based on the co-localization detection of DNA damage by an antibody against DNA damage markers such as gamma-H2AX and telomeres by the telomeric protein TRF2. Briefly, HCT116 cells were plated in 4-well chamber slides and after the cells attached to the surface, either 3 µM 6-thio-dG or 3 µM 6-thio-G was added to the medium at different time points (0, 30 min, 12 h, 24 h, 48 h, 72 h). Slides were rinsed once with PBS and fixed in 4% paraformaldehyde in PBS for 10 min. Then, cells were washed twice with PBS and permeabilized in 0.5% Nonidet-P40 in PBS, blocked with 0.5% Bovine Serum Albumin (BSA) and 0.2% fish gelatin in PBS for 30 min. gamma-H$_2$AX (mouse) (Millipore, Billerica, Mass.) was diluted 1:1000 and TRF2 (rabbit) (Abcam, Cambridge, Mass.) was diluted 1:200 in blocking solution and this primary Ab mixture was incubated on cells for 2 h. After three washes with PBST (1×PBS in 0.1% Triton) and 3 washes with PBS, cells were incubated with Alexaflour 488 conjugated goat anti rabbit (1:500) (Invitrogen, Grand Island, N.Y.) and Alexaflour 568 conjugated goat anti mouse (1:500) (Invitrogen) for 40 min, then washed six times with PBS. After drying, the slides were mounted with Vectashield mounting medium with DAPI (Vector Laboratories, Burlingame, Calif.). Images were captured with Deltavision wide-field microscope, then deconvoluted using Autoquant X3. TIFs were quantified using Imaris software.

Statistical Analysis

Comparisons of different groups for statistical significance were analyzed using a two-tailed, unpaired. Student t test. P value of 0.05 or less was considered significant.

Results

Effects of 6-thio-dG and 6-thio-G on cellular morphology

Figure 1B:
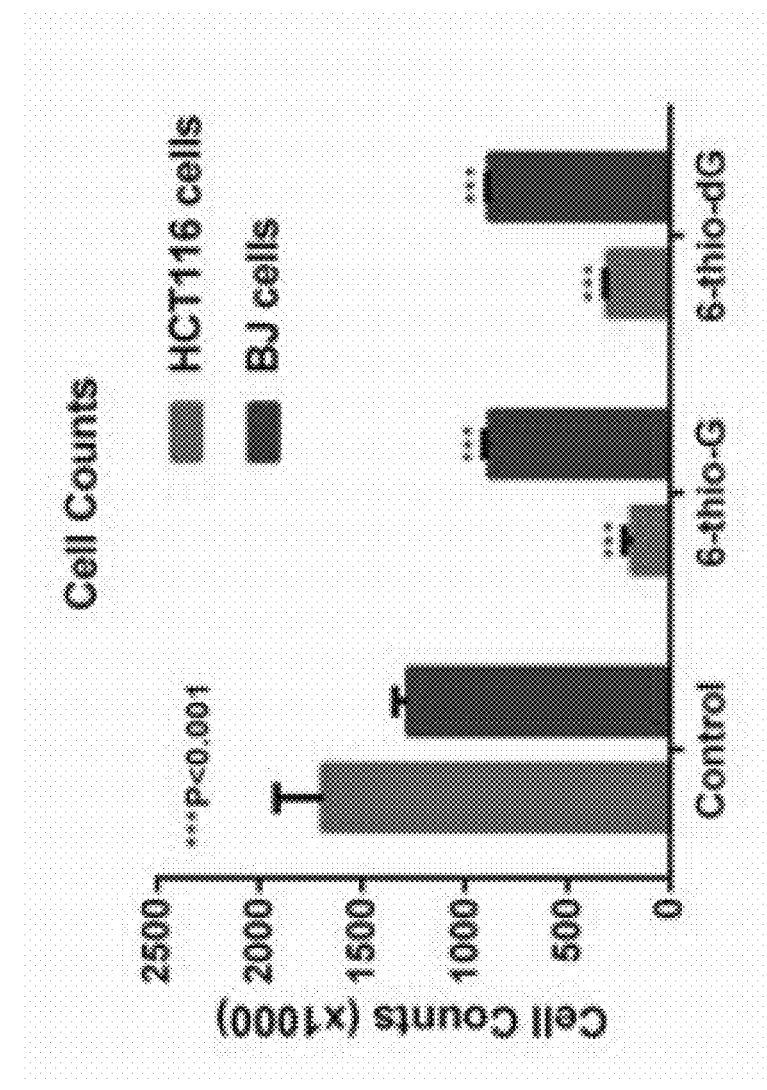
FIG. 1B. A graph demonstrating the cell counts of HCT116 and BJ cells treated with 6-thio-dG (3 μM) and 6-thio-G (3 μM) for 1 week (every 3 days). (Control; untreated)

Cancer HCT116 and normal BJ fibroblast cells were treated with 6-thio-dG (3 µM) and 6-thio-G (3 µM) twice during one week. Following one week of the treatment, cell morphology was monitored, and then the cells were collected and counted. FIG. 1B shows the results of the cell count. Treatment with 6-thio-dG resulted in death of the vast majority of HCT116 cells. and also changed their morphology, whereas the morphology and cell counts of normal BJ fibroblasts were only slightly affected.

6-Thio-dG, but not 6-Thio-G, Resulted in Progressive Telomere Shortening in Cancer Cells To determine if 6-thio-dG and 6-thio-G causes progressive telomere shortening, telomere lengths of treated cells were evaluated by TRF assay. Cancer HCT116 and normal BJ fibroblast cells were treated with 1 µM or 10 µM of 6-thio-dG for 1-12 weeks every 3 days. In addition, HCT116 cells were also treated with 1 µM or 10 µM 6-thio-G for 1-10 weeks every 3 days to determine if there is any effect of this molecule on telomeric length maintenance. The control was untreated. Each week samples were collected for TRF analysis at 1×10$^6$ cells/sample at 1, 5, and 12 weeks for cells treated with 6-thio-dG and 1, 5, and 10 for cells treated with 6-thio-G.

The results of the TRF assays showed that telomere shortening was detectable as early as one week and five weeks, with more dramatic telomeres shortening after 12 weeks of continuous 6-thio-dG treatment. At 12 weeks, both the 104 or 10 µM showed dramatic telomere shortening. At the same time, treatment with 6-thio-G did not result in any significant effects on telomere length of HCT116 cells after 10 weeks. This suggested that intracellular metabolic pathways of 6-thio-dG and 6-thio-G are different, and that 6-thio-dG is much more readily converted into the corresponding 5'-triphosphate, which is eventually being recognized by telomerase and incorporated into telomeres.

In addition, BJ fibroblast cells treated with 6-thio-dG or 6-thio-G (data not shown) for 10 weeks did not show enhanced telomere shortening, as compared to untreated control cells. When telomerase activity of HCT116 cells treated with 6-thio-dG or 6-thio-G was evaluated by TRAP assay, no inhibition of telomerase activity was observed for either. (For the TRAP assay, cells were treated with 1 and 10 µM 6-thio-dG every 3 days for 12 weeks. Each week samples were collected for TRAP analysis at 1×10$^5$ cells/sample. The control was an untreated sample.) This suggests that 6-thio-dG causes telomeric shortening independent from telomerase inhibition.

6-thio-dG and GRN163L show additive effects on telomere shortening

HCT116 cells were treated with either 10 µM 6-thio-dG alone for 12-16 weeks, or with 3 µM GRN163L alone for 11 weeks. Then, these long term 6-thio-dG treated surviving cells were cultured with a combination of 6-thio-dG (10 µM) and/or GRN163L (3 µM) for 2-4 additional weeks. FIG. 2 shows a table summarizing the types of treatment protocols tested. Treatment with GRN163L did not show any significant telomere shortening after 11 weeks as compared to the control. Yet, combination therapy produced additive, if not synergistic, effects on HCT116 cell telomere shortening. Specifically, the HCT116 cells were treated beyond the 12 weeks of 6-thio-dG treatment with either GRN163L only or GRN163L+6-thio-dG, for an additional 2 and 4 weeks to determine if there is an effect on telomere length. These cells cultured with 6-thio-dG beyond 12 weeks of treatment with GRN163L, whether alone or in combination, resulted in increased telomere shortening in HCT116 cells as compared with cells cultured with 6-thio-dG for 12, weeks, 14 weeks, and 16 weeks. These results suggest that combination therapy of 6-thio-dG and GRN163L may be more effective than the single agent therapy with either GRN163L or 6-thio-dG.

Treatment of telomerase positive cells only with 6-thio-dG or only with GRN163L id exhibit telomere shortening, as compared with the telomerase negative control cells. However, HCT116 cells treated with 6-thio-dG for 12 weeks and then continued to be treated with 6-thio-dG exhibited stabilized telomeres. In other words, the detected telomere lengths were approximately the same at 12 weeks and 16 weeks. In addition, when cells cultured with 6-thio-dG for 12 weeks were then returned to normal medium without drug for 2-4 weeks, the telomere remained about the same as after 12 week of 6-thio-dG treatment. This suggests that 6-thio-dG treatment does not allow cells to reverse its effects on telomeric lengths for at least 2 to 4 weeks.

Notably, telomerase inhibitors do not immediately cause cell death. By binding to telomerase and inhibiting its enzymatic activity telomerase cannot maintain telomere homeostasis. Indeed, it can take several months to drive the already short telomeres in cancer cells to become so short that they initiate cell death (apoptosis). Thus, with classic telomerase inhibitors there is a substantial lag phase before cancer cells die. As demonstrated by the present study of GRN163L, there was a delay in telomere shortening for GRN163L as compared to 6-thio-dG. (FIG. 3A (telomerase inhibition) and FIG. 3B (telomere altering (such as uncapping) in telomerase positive cells) show a comparison of this respective lag times in causing cell death.) The 6-thio-dG shortened this lag period considerably since the mechanism of causing apoptosis is to have 6-thio-dG be converted to 6-thio-dGTP in the cells. Such converted compounds are a good and specific substrate for telomerase and can be incorporated into the telomeres. Thus, compounds of the present disclosure do not inhibit telomerase but are an immediate telomere chain terminator (that is dependent on the presence of telomerase) that will be recognized as damaged DNA and will result in rapid initiation of apoptosis.

6-Thio-dG, but not 6-Thio-G, Resulted in Telomere Dysfunction Induced Foci (TIFs) in Telomerase Expressing Cells Normal BJ cells and telomere expressing BJ-hTERT cells were seeded in chamber slides. Following cell attachment, 6-thio-dG (10 μM) and 6-thio-G (10 μM) were added to fresh medium of each cell type. To test if 6-thio-dG and 6-thio-G cause telomere dysfunction in normal cells as compared to telomere expressing cells, TIF analysis was conducted. A control was used for each cell type as well, where DMSO was added to fresh medium of each cell type. Using combination of gamma-H2AX and TRF2 immuno-staining we were able to distinguish between genomic DNA damage and telomere specific damage after 48 hours. The results are shown in Table 1. As shown, the 6-thio-dG induced telomere induced foci in BJ-hTERT cells and exhibited more specificity for telomerase expressing cells over normal cells. In comparison, 6-thio-G did not induce telomere induced foci. This demonstrates that only telomerase expressing cells will be affected by 6-thio-dG. These include almost all human cancer cells and certain human diseases involving acute and chronic inflammation.

TABLE 1

| Cell types/Drug treatment | Number of nuclei scored | >4 TIFs per nucleus background subtracted |
|---|---|---|
| BJ-hTERT/DMSO control | 104 | 0 |
| BJ-hTERT/6-thio-G | 94 | 0 |
| BJ-hTERT/6-thio-dG | 97 | 14 |
| BJ/DMSO control | 102 | 0 |
| BJ/6-thio-G | 101 | 0 |
| BJ/6-thio-dG | 100 | 2 |

6-Thio-dG Treatment Results in Telomere Dysfunction in Cancer Cells

Figure 4:
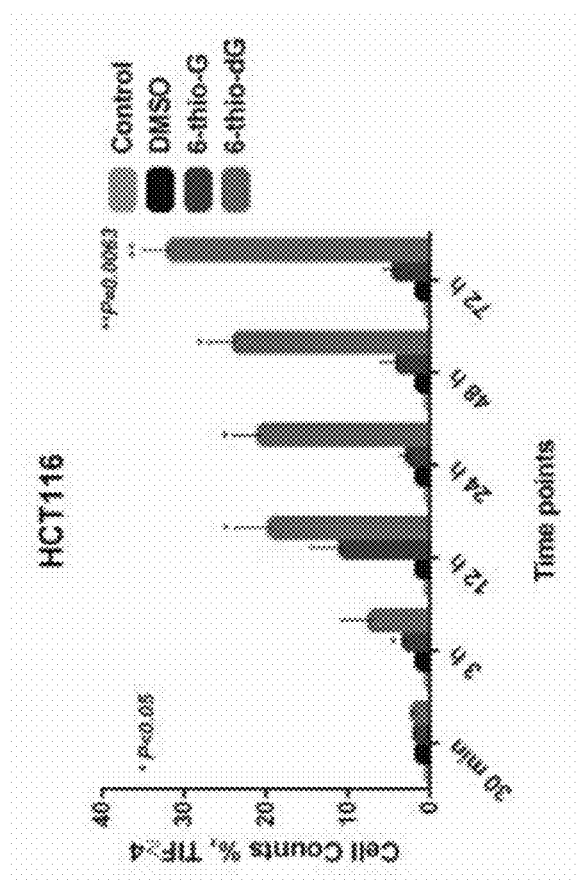
FIG. 4. DNA damage foci per cell. HCT116 cells treated with 6-thio-dG (3 μM) and 6-thio-G (3 μM) (n=75, SDs from two independent experiments). P=0.003, *P=0.0005, *P=0.0141 (6-thio-G versus 6-thio-dG), in the unpaired Student t test. ns, not significant differences in the unpaired Student t test. (Control; untreated).
Figure 5:
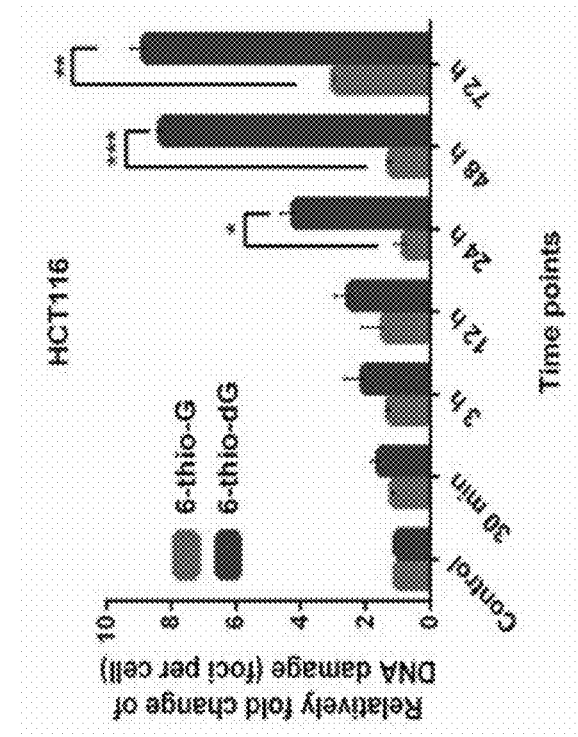
FIG. 5. TIF index (percentage of TIF positive cells) of HCT116 cells treated with 6-thio-dG (3 μM) or 6-thio-G (3 μM). Cells with four or more gamma-H2AX foci colocalizing with TRF2 were scored as TIF positive by Imaris software (n=75, SDs from two independent experiments). *P<0.05, **P=0.0063 (compared with vehicle control), in the unpaired Student t test. ns, not significant differences in the unpaired Student t test. (Control; untreated).

Cancer HCT116 cells were seeded in chamber slides. Following cell attachment, 6-thio-dG (3 μM) and 6-thio-G (3 μM) were added to fresh medium at various time points (0, 30 min, 2 h, 12 h, 24 h, 48 h, 72 h). To test if 6-thio-dG and 6-thio-G cause telomere dysfunction in cancer cells, TIF analysis was conducted. Using combination of gamma-H2AX and TRF2 immuno-staining we were able to distinguish between genomic DNA damage and telomere specific damage. 6-thio-dG treatment causes a 2.8-fold increase in telomeric DNA damage as compared to 6-thio-G after 72 h (FIG. 4). In addition to the increase in telomere damage by 6-thio-dG, there was also an overall increase in genomic DNA damage compared to 6-thio-G (FIG. 5). Co-localization of gamma-H2AX and TRF2 show the existence of dysfunctional telomeres, which can leave chromosome ends uncapped and can induce DNA damage responses, such as cell cycle arrest, senescence, apoptosis and chromosome end fusions.

6-Thio-Dg Treatment Decreases the Survival and Viability of HCT116 Cells

Figure 6A:
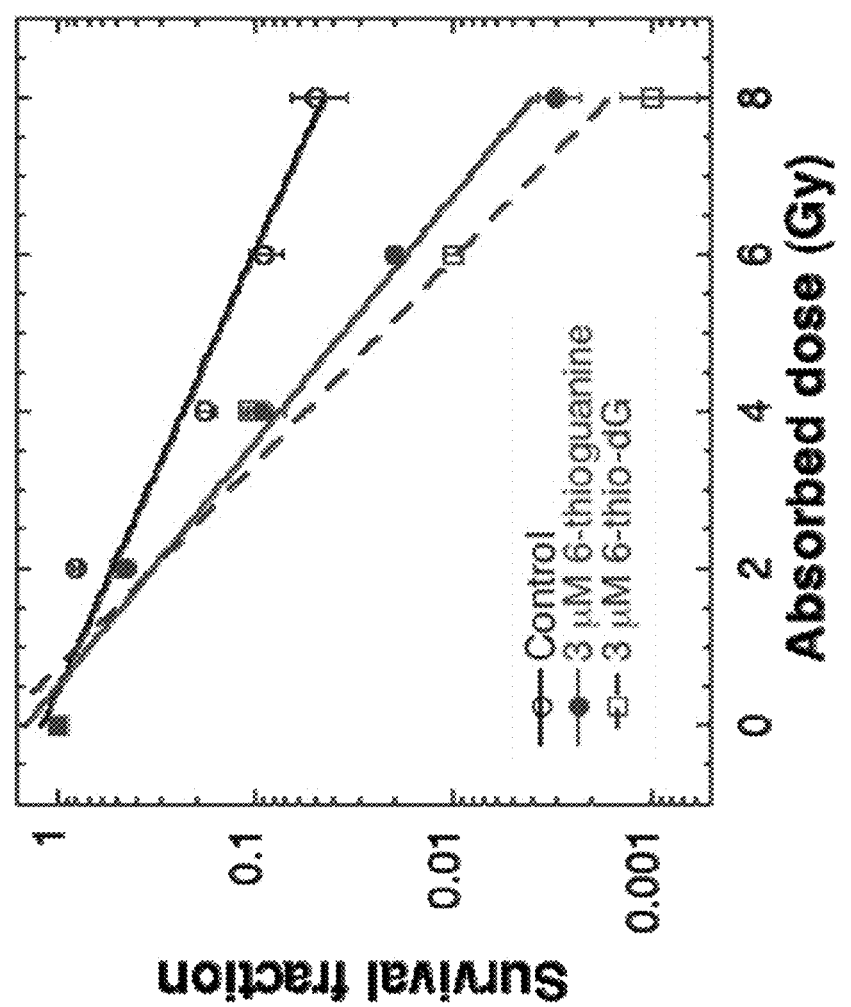
FIGS. 6A and 6B. (A) Line graph showing the survival fraction of HCT116 treated with 6-thio-dg (3 μM) and 6-thio-G (3 μM), and after 72 hours, were irradiated with various doses of ionizing radiation. Following the treatment cells were seeded at different densities and the cultured for 10 days. (B) Line graph showing cell viability determined using a cell titer glow luminescent assay.
Figure 6B:
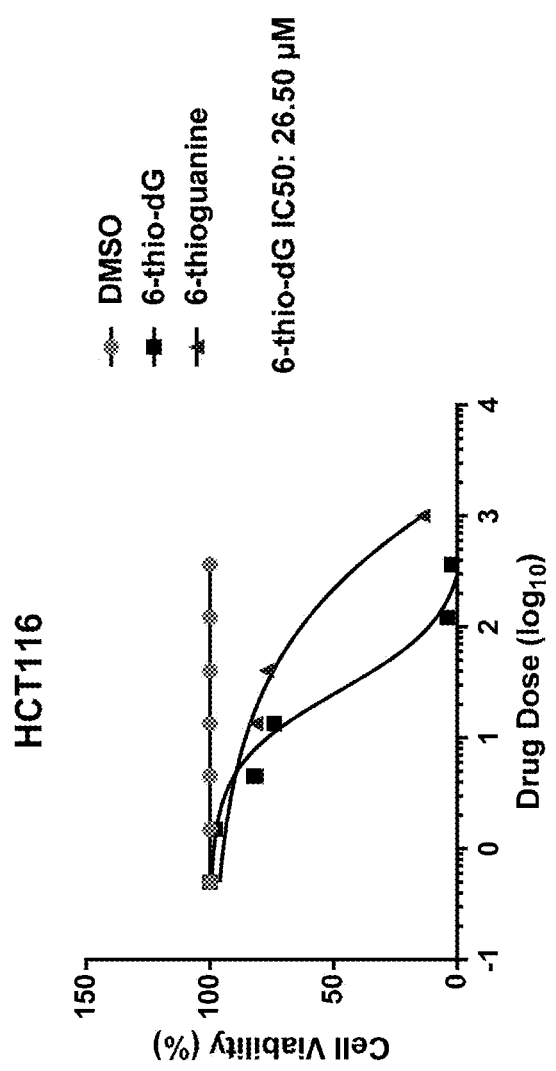

As shown in FIG. 6A, the survival fraction of HCT116 cells treated with 6-thio-dG is lower than cells treated with 6-thio-G. HCT116 cells were treated with 6-thio-dg (3 μM) and 6-thio-G (3 μM), and after 72 hours, were irradiated with various doses of ionizing radiation. Following the treatment cells were seeded at different densities and the cultured for 10 days. As shown in FIG. 6B, cell viability of HCT116 cells treated with 6-thio-dG is lower than cells treated with 6-thio-G. Cell viability was determined using a cell titer glow luminescent assay.

GI 50 Values in a Normal Cell Line and a Panel of Cancel Cell Lines Demonstrate that 6-Thio-dG was More Effective at Lower Dosages Against a Variety of Cancer Cell Lines than 6-Thio-G Cells of each type listed in Table 2 were seeded in chamber slides. GI 50 values were determined for a panel cancer cell lines and a normal BJ cell line for both 6-thio-dG and 6-thio-G. As shown in Table 2, the GI 50 values were slightly higher for 6-thio-G as compared with 6-thio-dG in all the cancer cell lines except the H2087, where it was equal. Thus, 6-thio-dG was more effective at a lower dosage against a variety of cancer cell lines compared to 6-thio-G. This suggests that 6-thio-dG is a more effective chemotherapeutic agents compared to an already approved compound, 6-thio-G due to an additional mode of action. In xenograft and mouse toxicity studies described in the next section, 6-thio-dG is not only more effective in reducing tumor burden but with less toxicity (e.g. less weight loss).

TABLE 2

| Cell Type | 6-thio-dG (GI 50, μM) | 6-thio-G (GI 50, μM) |
|---|---|---|
| BJ | >100 | >100 |
| HCT116 | 1.0 | 1.2 |
| A549 | 2.1 | 2.3 |
| H2882 | 0.4 | 0.6 |
| HCC2429 | 0.6 | 0.7 |
| HCC827 | 0.8 | 1.7 |
| HCC15 | 0.8 | 1.1 |
| H2087 | 0.9 | 0.9 |
| HCC4017 | 0.9 | 2.0 |
| HCC515 | 2.4 | 4.9 |
| H2009 | 2.6 | 3.3 |

6-Thio-Dg Treatment Decreases the Rate of Tumor Growth in Xenograft Animal Models with HCT116 and A549 Cells.

Figure 7A:
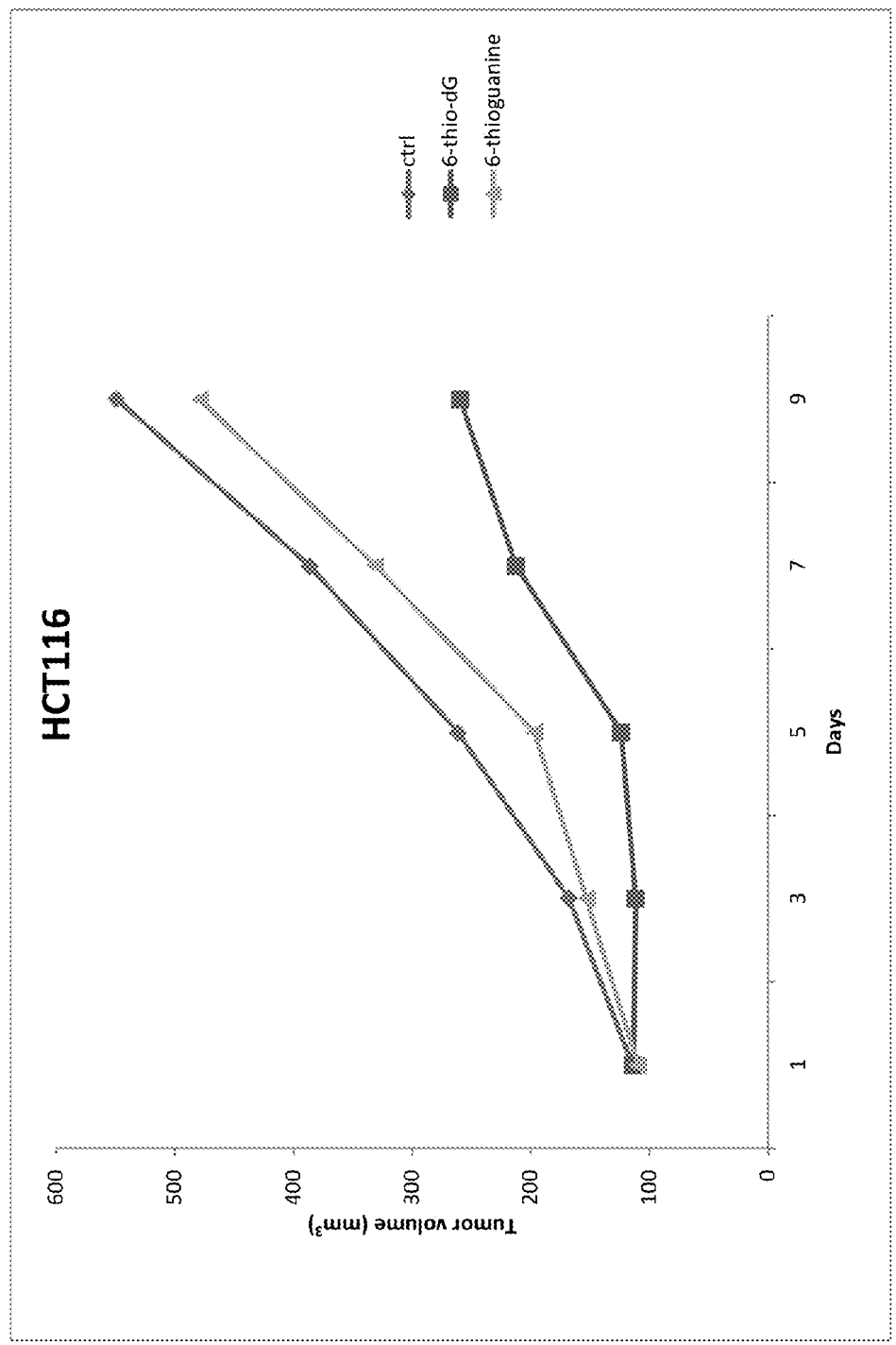
FIGS. 7A and 7B. (A) Line graph showing a reduction in the rate of tumor growth in Xenograft animal models with HCT116. (B) Line graph showing a reduction in the rate of tumor growth in Xenograft animal models with A549 cells.

Doses of 2 mg/kg of 6-thio-dG and 2 mg/kg of 6-thio-G were IP injected every two days for a total of 6 injections into mice. DMSO injections were used for the control. The volume of the tumor was measured. FIG. 7A shows that the rate of tumor growth was less for the animal models with HCT116 cells receiving the 6-thio-dG injections.

Figure 7B:
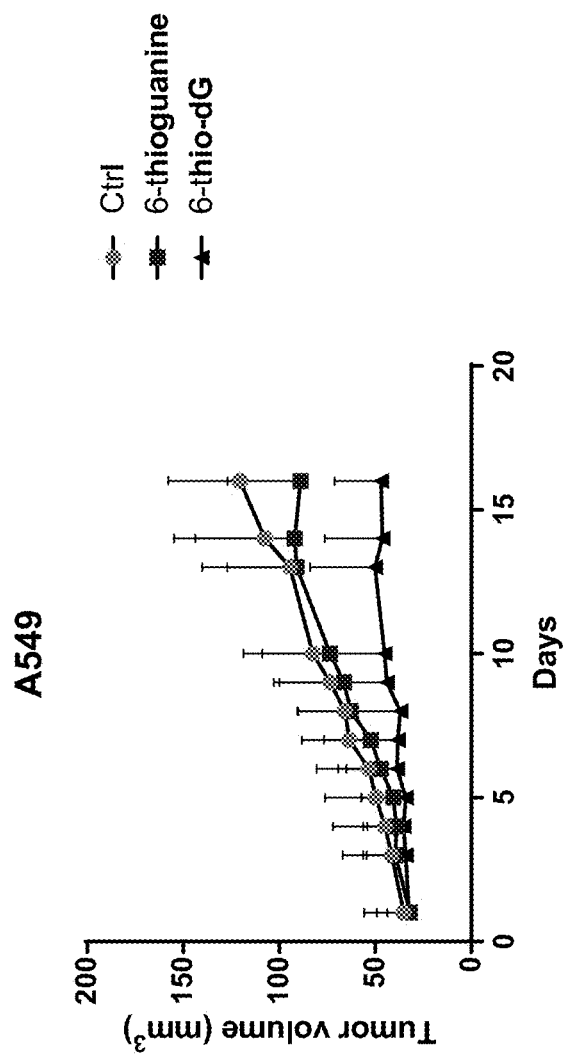

Doses of 2.5 mg/kg of 6-thio-dG and 2.5 mg/kg of 6-thio-G were injected every day into mice after tumor implantation and providing time for tumor initiation. DMSO injections were used for the control. The volume of the tumor was measured. FIG. 7B shows that the rate of tumor growth was less for the animal models with A549 human lung cancer cells receiving the 6-thio-dG injections compared to the control and 6-thio-G treated mice. In addition, upon a histology comparison of the residual tumors, the residual 6-thio-dG tumors were mostly fibrotic and often associated with apoptotic and inflammatory cells, whereas the residual 6-thio-G and control tumors exhibited mostly "healthy" growing cancerous cells.

Toxicity Testing in Rats

Six rats were treated with 15 mg of 6-thio-dG/kg of body weight every two days. One rat died after 6 injections, the remaining five mice showed no signs of impaired function. Another 5 rats were treated with 50 mg of 6-thio-dG/kg of body weight every other day. All rats died after 12 days.

Toxicity-Weight Loss Testing in WT Mice

Figure 8A:
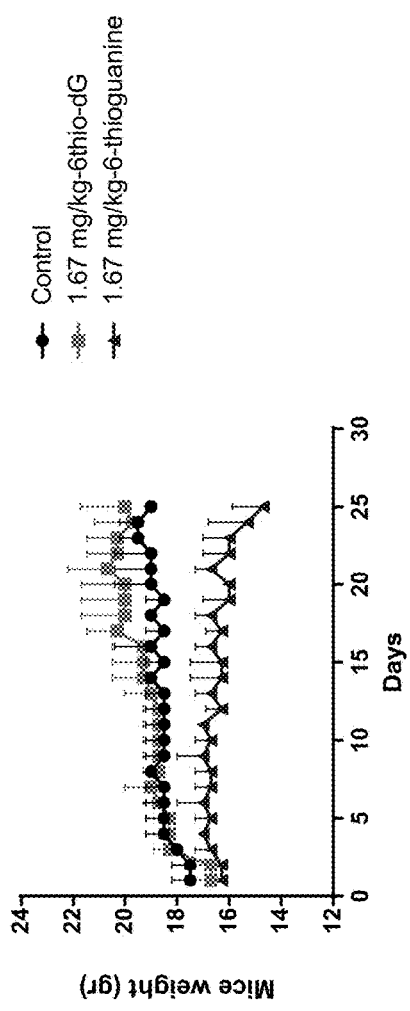
FIGS. 8A and 8B. (A) Line graph showing the weight loss in WT mice models models receiving 1.67 mg/kg of 6-thio-dG or 6-thio-G, as compared to a control. (B) Line graph showing the weight loss in WT mice models receiving 5 mg/kg of 6-thio-dG or 6-thio-G, as compared to a control.
Figure 8B:
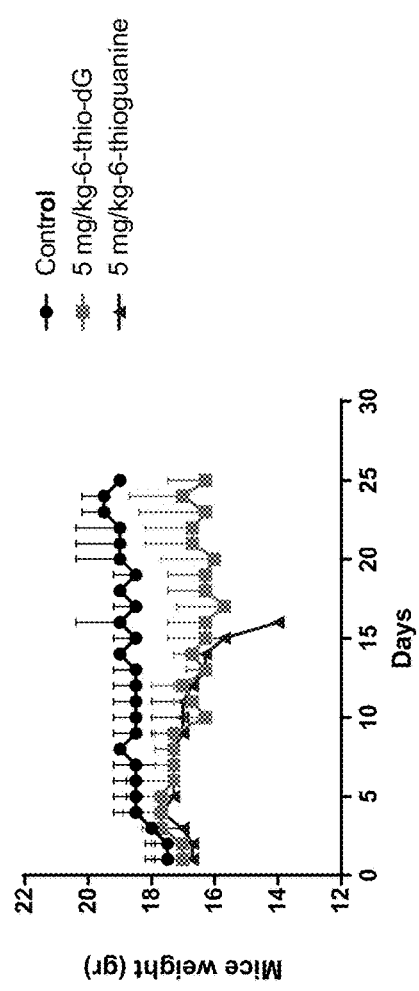

Six WT mice were treated with 1.67 mg of 6-thio-dG/kg of body weight daily. Six WT mice were treated with 1.67 mg of 6-thio-G/kg of body weight daily. Six WT mice were treated with 5 mg of 6-thio-dG/kg of body weight daily. Six WT mice were treated with 5 mg of 6-thio-G/kg of body weight daily. The mice were given the appropriate dosage and weighed daily for 25 days. The results are shown in FIGS. 8A and 8B. For the mice administered the lower 1.67 mg/kg dose, an example of an effective cancer dose, no weight loss was observed for those treated with 6-thio-dG. In comparison, the mice receiving 6-thio-G at the same dose lost between 1-2 grams (6-12% of initial weight) over the course of the 25 day treatment. For the mice administered the higher 5 mg/kg dose (a 2-3 fold increase over an effective cancer dose), only modest weight loss was observed for those treated with 6-thio-dG. In comparison, the mice receiving 6-thio-G at the same dose loss around 2 grams and all mice died by the 15$^{th}$ day of treatment. Importantly, these results in normal mice suggest that expected toxicities associated with treating cancer patients 6-thio-dG are expected to be significantly less compared to the already approved 6-thio-G compound. In addition, there is a significant tumor reduction effect of 6-thio-dG at ~3-fold lower doses that do not cause weight loss in mice.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. A method of treating a telomerase-expressing lung cancer cell or colon cancer cell characterized by an overactivation of telomerase in a subject in need thereof with lung cancer or colon cancer, comprising administering a pharmaceutical composition comprising a compound analogue according to Formula III:

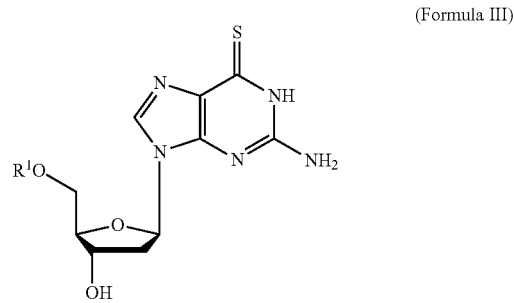

(Formula III)

wherein $R^1$ is H a pharmaceutically acceptable salts or a polymorph thereof;

wherein the pharmaceutical composition is administered in an amount effective to reduce stability of telomere length and to induce cell death in the telomerase-expressing lung cancer cell or colon cancer cell.

2. The method of claim 1, wherein the pharmaceutical composition is administered in an amount between 0.5-3 mg per 1 kg of the subject per day.

3. The method of claim 1, wherein the administering of the pharmaceutical composition is at least twice per week for at least 2 weeks, at least 4 weeks, at least 6 weeks, at least 8 weeks, or at least 12 weeks.

4. The method of claim 1, wherein the administering of the pharmaceutical composition is orally or by injection.

5. The method of claim 1, wherein the administering of the pharmaceutical composition is by intratumoral injection.

6. The method of claim 1, wherein the subject is a human being.

7. The method of claim 1, wherein the telomerase-expressing lung cancer cell or colon cancer cell characterized by overactivation of telomerase is a telomerase-expressing tumor cell.

8. The method of claim 7, wherein the amount effective to reduce stability of telomere length and induce cell death in the telomerase-expressing lung cancer cell or colon cancer cell effects a reduction in tumor size of a lung tumor or colon tumor comprising the telomerase-expression lung cancer

SEQUENCE LISTING

<160> NUMBER OF SEQ ID NOS: 1

<210> SEQ ID NO 1
<211> LENGTH: 13
<212> TYPE: DNA
<213> ORGANISM: Artificial Sequence
<220> FEATURE:
<223> OTHER INFORMATION: GRN163L Imetelstat sodium thio-phosphoramidate oligonucleotide

<400> SEQUENCE: 1
tagggttaga caa                                                          13 cell or colon cancer cell or a reduction in tumor growth rate of a lung tumor or colon tumor comprising the telomerase-expressing lung cancer cell or colon cancer cell.

* * * * *